US00PP24904P3

(12) United States Plant Patent
Olesen

(10) Patent No.: US PP24,904 P3
(45) Date of Patent: Sep. 23, 2014

(54) MINIATURE ROSE PLANT NAMED 'POULPAL040'

(50) Latin Name: ***Rosa* hybrid**
Varietal Denomination: Poulpal040

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 180 days.

(21) Appl. No.: 13/507,013

(22) Filed: May 31, 2012

(65) Prior Publication Data

US 2013/0326748 P1 Dec. 5, 2013

(51) Int. Cl.
*A01H 5/00* (2006.01)

(52) U.S. Cl.
USPC ..... Plt./117

(58) Field of Classification Search
CPC ..... A01H 5/0222
USPC ..... Plt./117, 124, 144
See application file for complete search history.

*Primary Examiner* — June Hwu

(57) ABSTRACT

A new miniature rose plant that has abundant, white flowers and attractive foliage. The variety successfully propagates from softwood cuttings and is suitable for year-round production in commercial glasshouses. This new and distinct variety has shown to be uniform and stable in the resulting generations from asexual propagation.

3 Drawing Sheets

Botanical designation: *Rosa* hybrid.
Variety denomination: 'Poulpal040'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpal040', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpal040' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal040' was selected by the inventor as a single plant from the progeny of the hybridization in 2006.

Asexual reproduction of 'Poulpal040' by cuttings was first done by Mogens N. Olesen in the nursery in Fredensborg, Denmark in 2007. This initial and other subsequent propagations conducted in controlled environments have demonstrated that the characteristics of 'Poulpal040' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal040' on plants which are 3 months of age.

Specifically illustrated in the drawing are FIG. 1 open flowers at various stages of development, FIG. 2 flower buds, leaves and stems, FIG. 3, open flowers on the plant.

DETAILED DESCRIPTION OF THE VARIETY

Figure 1:
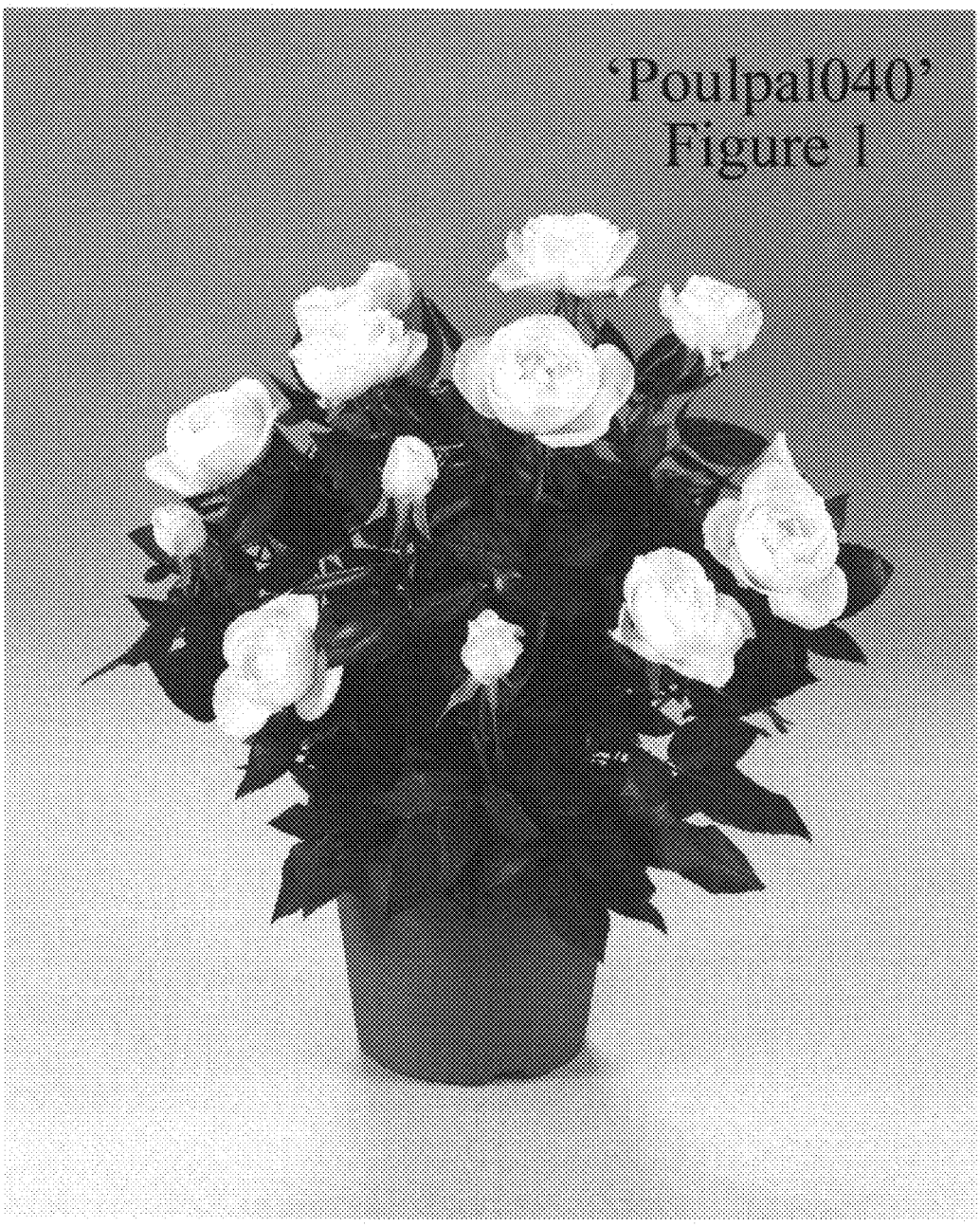
Figure 2:
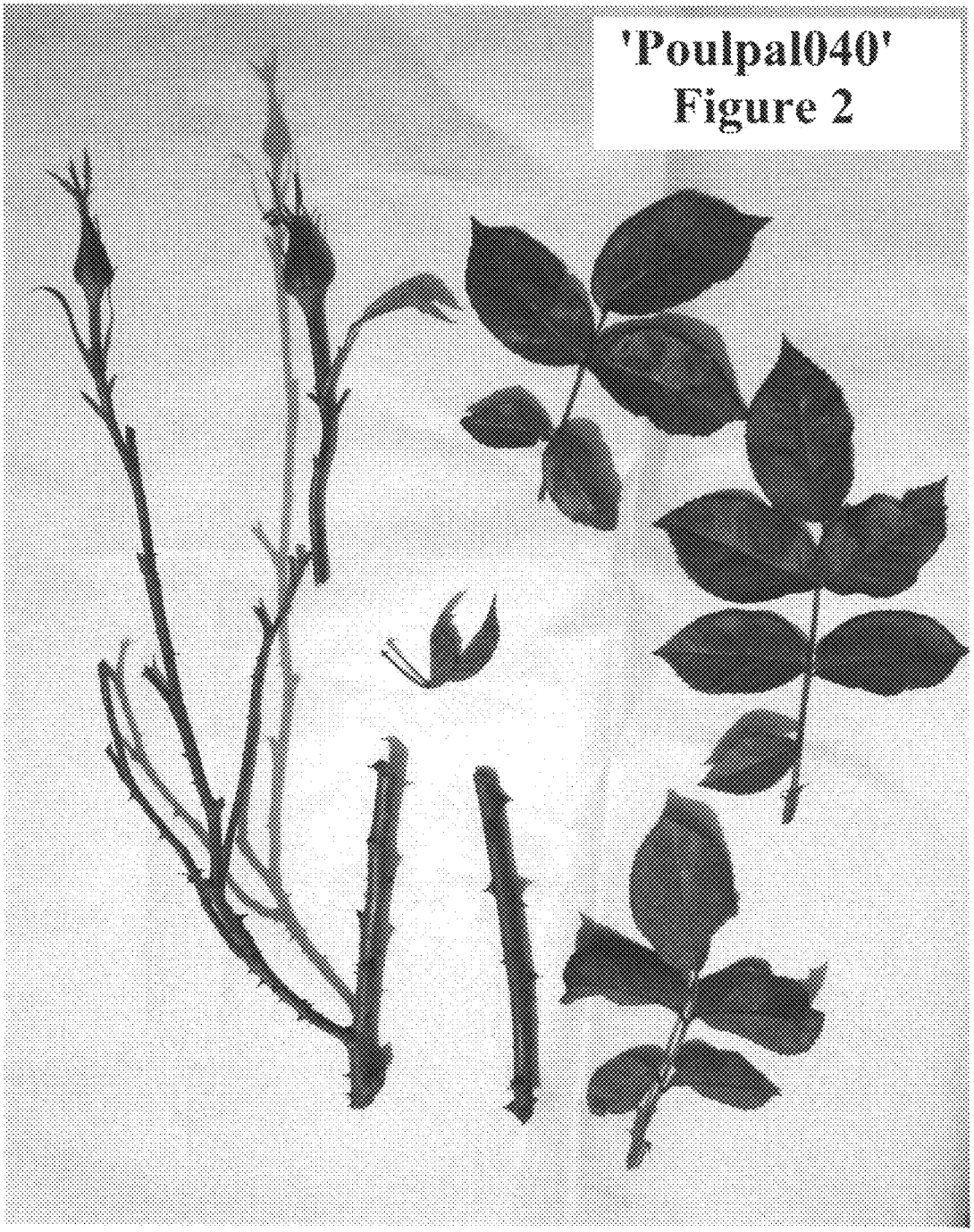
Figure 3:
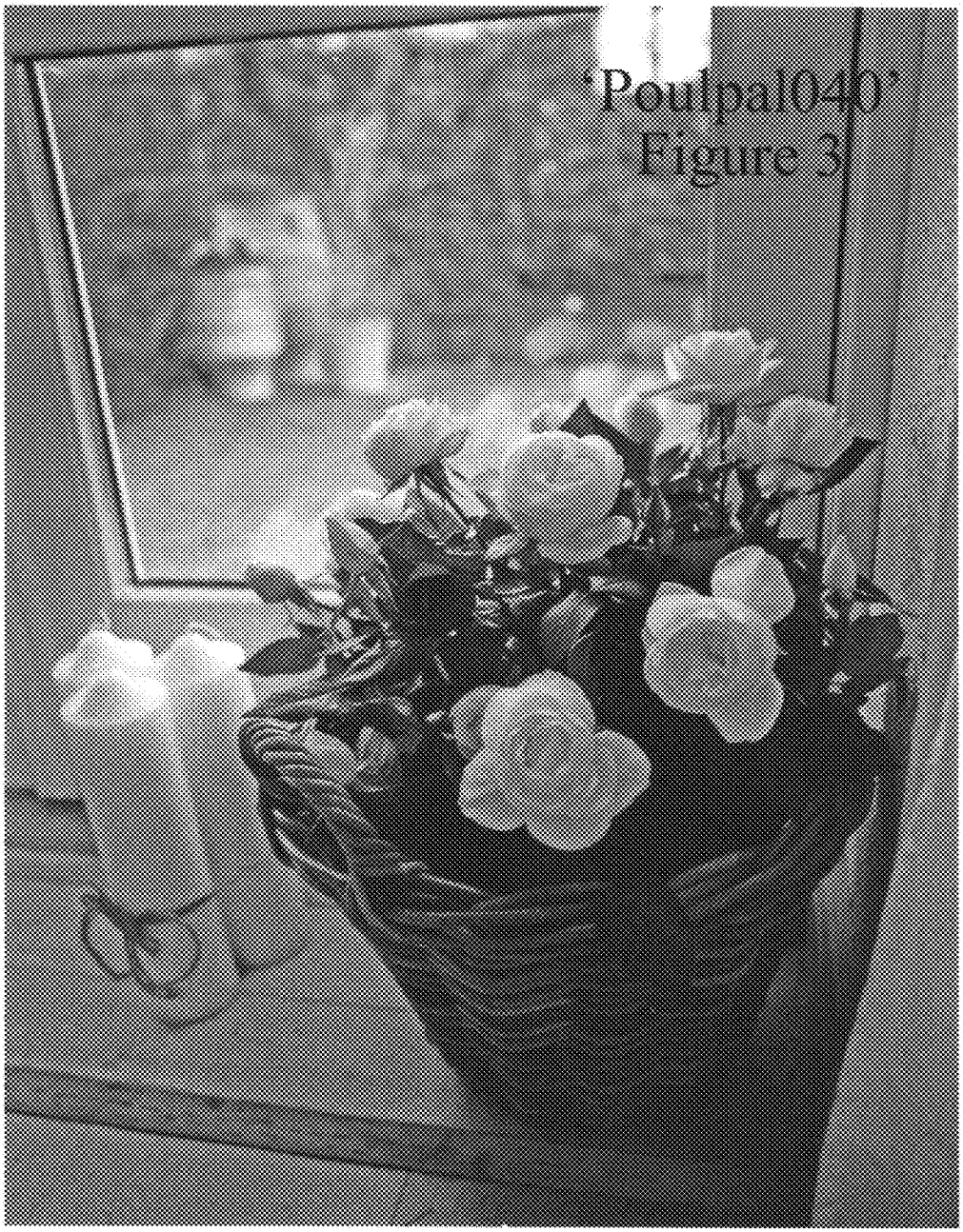

The following is a description of 'Poulpal040', as observed in its growth in a field nursery in Corvallis, Oreg. Observed plants are 2 years of age and were cultivated on their own roots. Color references are made using The Royal Horticultural Society (London, England) Colour Chart, 2001, except where common terms of color are used.

For a comparison, several physical characteristics of the rose variety 'Poulgret', U.S. Plant Pat. No. 10,729 are compared to 'Poulpal040' in Chart 1.

| | 'Poulpal040' | 'Poulgret' |
|---|---|---|
| General flower color | White Group 155B | White Group 155B |
| Flower diameter | 70 mm average | 50 to 60 mm |
| Coloration of the underside of sepals | Yellow-Green Group 144A with strong intonations of Greyed-Red Group 178A. | Green Group 138A to 138B |

FLOWER AND FLOWER BUD

Blooming habit: Continuous.

Flower bud:

*Size*.—Upon opening, 25 mm in length from base of receptacle to end of bud. 16 mm in diameter.

*Bud form*.—Ovate.

*Bud color*.—As sepals unfold, petals are green white.

Sepals:

*Under surface*.—Color: Yellow-Green Group 144A with strong intonations of Greyed-Red Group 178A. Texture: Smooth.

*Upper surface*.—Smooth texture. Shape: Apex: Cirrhose. Base: Flat at union with receptacle. Margins: Margins have moderate to strong foliaceous appendages on three of the five sepals. Size: 45 to 50 mm long by 8 mm wide.

*Receptacle*.—Surface Texture: Smooth. Shape: Funnel shaped. Size: 8 mm tall and 8 mm wide. Color: Yellow Green Group 144A.

*Pedicel*.—Surface: Somewhat rough with many stipitate glands. Length: 25 mm on average. Diameter: 3 to 4 mm. Color: Yellow-Green Group 144A with anthocyanic pigments the color of Greyed-Orange Group 166B. Strength: Medium strength.

*Borne*.—Singly.

Flower bloom:

*Fragrance*.—None.

*Duration*.—As a pot plant, flowers last up to 28 days.

*Size*.—Flower diameter is about 70 mm when open. Flower depth is about 35 mm.

*Form*.—General shape is an open cup with petals that curve outward from the center.

Color:

*General tonality*.—On open flower, White Group 155B.

*Upon opening, petals*.—Petals are White Group 155B. on the upper surface and White Group 155B. on the lower surface.

*After opening, petals*.—Petals are White Group 155B. on the upper surface and White Group 155B. on the lower surface.

Petals:

*Petal reflex*.—Weak.

*Margin*.—Entire, uniform.

*Shape*.—Generally broad and elliptic. Apex shape: Rounded. Base shape: Acute.

PLANT

Plant growth: Upright. Plants are 70 to 75 cm in height, and 60 cm wide.

Stems:

*Color*.—Juvenile growth: Yellow-Green Group 146C with strong anthocyanic intonations the color of Greyed-Purple Group 183C. Mature growth: Yellow-Green Group 146B.

*Length*.—Canes are 40 cm from the base of the plant to the flowering portion.

*Diameter*.—6 to 7 mm.

*Internodes*.—On mature canes, there is an average distance of 32 mm between nodes.

*Surface texture*.—Young and mature wood is rough with a moderate quantity of small prickles.

Large prickles: Incidence: 8 per 10 cm of stem. Size: Average length, 7 mm. Color: Juvenile prickles are Greyed-Purple Group 183B. Mature prickles are Greyed-Orange Group 164C. Shape: Concave on the upper and lower surface.

Plant foliage:

*Compound leaf size*.—170 mm (l) by 115 mm (w).

*Quantity*.—2 leaves per 10 cm of stem.

*Color of juvenile foliage*.—Upper Leaf Surface: Yellow-Green Group 146B. Lower Leaf Surface: Greyed-Red Group 178A.

*Color of mature foliage*.—Upper Leaf Surface: Yellow-Green Group 146A. Lower Leaf Surface: Yellow-Green Group 146B.

Plant leaves and leaflets:

*Stipules*.—Size: About 20 mm in length. Shape: Linear, slightly broad based with outward extending apecies. Margins: Finely serrated. Color: Yellow-Green Group 144A.

*Petiole*.—Length: 33 mm on average. Diameter: About 2 mm. Upper surface: Greyed-Purple Group 185A. Lower surface: Yellow-Green Group 144B and Greyed-Purple Group 185A. Small prickles observed.

*Rachis*.—Length: 50 mm on average. Diameter: About 2 mm. Upper surface: Greyed-Purple Group 185A. Lower surface: Yellow-Green Group 144B and Greyed-Purple Group 185A. Small prickles observed.

*Leaflet*.—Number of leaflets: 5 on normal leaves in middle of the stem. Size: 65 mm in length by 40 mm wide. Margin: Serrate. General Shape: Elliptical. Apex Shape: Mucronate. Base Shape: Round. Texture: Smooth on upper and lower surface. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa,* downy mildew *Peronospora sparsa,* rust *Phragmidium* spp., black spot *Diplocarpon rosae,* and *Botrytis cinerea* under normal growing conditions.

The invention claimed is:

1. A new and distinct variety of rose plant of the miniature class named 'Poulpal040', substantially as illustrated and described herein, due to its abundant, white flowers, vigorous growth, compact habit, suitability for production from softwood cuttings in pots, and durable flowers and foliage that make the variety suitable for distribution in the floral industry.

* * * * *

'Poulpa1040'

'Poulpal040'

'Poulpal040'